(12) United States Patent
Zheng (10) Patent No.: US 9,599,566 B2
(45) Date of Patent: Mar. 21, 2017

(54) METHOD FOR MEASURING POLYMER CONCENTRATION IN WATER SYSTEMS

(71) Applicant: Ecolab USA Inc., St. Paul, MN (US)

(72) Inventor: Hua Zheng, Aurora, IL (US)

(73) Assignee: Ecolab USA Inc., St. Paul, MN (US)

( * ) Notice: Subject to any disclaimer, the term of this patent is extended or adjusted under 35 U.S.C. 154(b) by 0 days.

(21) Appl. No.: 15/088,609

(22) Filed: Apr. 1, 2016

(65) Prior Publication Data

US 2016/0290929 A1    Oct. 6, 2016

Related U.S. Application Data (60) Provisional application No. 62/142,098, filed on Apr. 2, 2015.

(51) Int. Cl.
   G01N 21/77    (2006.01)
   G01N 33/18    (2006.01)
   G01N 21/25       (2006.01)

(52) U.S. Cl.
   CPC .......... G01N 21/77 (2013.01); G01N 33/182 (2013.01); G01N 21/251 (2013.01); G01N 2021/7786 (2013.01)

(58) Field of Classification Search
   CPC ...... G01N 33/18; G01N 33/182; G01N 21/25; G01N 21/251; G01N 21/272; G01N 21/29; G01N 21/77; G01N 21/78; G01N 2021/7786; Y10T 436/14555
   USPC ..... 436/96, 164, 166, 171; 422/82.05, 82.09
   See application file for complete search history.

(56) References Cited

U.S. PATENT DOCUMENTS

| | | | | |
|---|---|---|---|---|
| 4,894,346 A | * | 1/1990 | Myers | G01N 31/22 436/129 |
| 5,120,661 A | * | 6/1992 | Baker | C02F 1/685 436/164 |
| 5,654,198 A | * | 8/1997 | Carrier | G01N 21/31 436/164 |
| 6,214,627 B1 | * | 4/2001 | Ciota | G01N 31/22 422/423 |
| 9,228,986 B2 | * | 1/2016 | Xiao | G01N 21/78 |
| 2004/0055965 A1 | | 3/2004 | Hubig et al. | |
| 2005/0238536 A1 | * | 10/2005 | Striepeke | G01N 33/50 422/68.1 |
| 2006/0142170 A1 | | 6/2006 | Jaralla | |
| 2007/0092973 A1 | | 4/2007 | Potyrailo et al. | |
| 2008/0295581 A1 | * | 12/2008 | Zhang | G01N 21/78 73/61.43 |
| 2008/0299665 A1 | * | 12/2008 | Xiao | G01N 21/78 436/85 |
| 2011/0003391 A1 | * | 1/2011 | Boyette | C08J 5/18 436/85 |

FOREIGN PATENT DOCUMENTS

WO    WO 2011/002642 A1    1/2011

OTHER PUBLICATIONS

Liu et al. Spectrochimica Acta Part A, vol. 64, 2006, pp. 817-822.*
Nishida et al. Colloid & Polymer Science, vol. 252, 1974, pp. 392-395.*
Israel Patent Office, International Search Report in International Patent Application No. PCT/US2016/025494, Jul. 5, 2016, 3 pp.
Israel Patent Office, Written Opinion in International Patent Application No. PCT/US2016/025494, Jul. 5, 2016, 6 pp.

* cited by examiner

*Primary Examiner* — Maureen Wallenhorst
(74) *Attorney, Agent, or Firm* — Leydig, Voit & Mayer, Ltd.

(57) ABSTRACT

The invention provides a method for measuring the concentration of anionic polymers in an industrial water system. Specifically, the concentration of anionic polymer can be measured by combining an indicator dye composition that includes an acridine compound or a salt thereof to a water sample and measuring the absorbance of the mixture. The concentration can be determined by comparing the absorbance of the mixture to absorbance values on a pre-determined calibration curve. The dosage of anionic polymer can be optionally adjusted based on the concentration.

19 Claims, 3 Drawing Sheets

METHOD FOR MEASURING POLYMER CONCENTRATION IN WATER SYSTEMS

CROSS-REFERENCE TO RELATED APPLICATIONS

This patent application claims the benefit of U.S. Provisional Patent Application No. 62/142,098, filed Apr. 2, 2015, which is incorporated by reference.

FIELD OF INVENTION

This invention is directed to a method of using an indicator dye to monitor anionic polymers in industrial water systems.

BACKGROUND OF THE INVENTION

Industrial water systems typically contain charged contaminants that are prone to precipitation from water as well as accumulation on industrial equipment surfaces. Common water contaminants such as calcium, iron, magnesium, barium, and aluminum, when present in feed water, are the major cause of scaling and corrosion in industrial water systems. Scaling and corrosion of system components can cause heat exchange inefficiency, fluid flow impedance, and bursting of pipes, potentially resulting in process shutdowns and production time loss. The time and financial loss associated with scaling and corrosion has resulted in the use of chemical treatments to reduce the presence of problematic metal contaminants in industrial water systems.

Chemical treatments are commonly used to control, reduce, and sometimes prevent the development of scale and corrosion. Chemical scale inhibitors act by interfering with crystallization, attachment, and/or deposit consolidation of water contaminants. In particular, anionically charged polymers (i.e., anionic polymers) can act as anti-scaling agents by removing dissolved and particulate cationic metals from water. The effectiveness of the anionic polymer is optimal when the polymer is maintained at an acceptable level. If the level of anionic polymer is too low, the amount of scaling and corrosion will increase. However, employment of an excess amount of anionic polymer results in unnecessary costs. Thus, the polymer treatment must be carefully monitored and controlled using accurate methods.

Spectroscopic methods in combination with indicator dyes can be used to detect and monitor the concentration of anionic polymer treatments in industrial water. When anionic polymers are exposed to an indicator dye capable of associating with the polymer, a complex results which can undergo spectroscopic analysis using ultraviolet, visible, or infrared light to ascertain the amount of polymer in the water system.

While many existing indicator dyes are useful in monitoring anionic polymer concentration, some suffer from disadvantages including high sensitivity to testing conditions and instability in aqueous solutions. Thus, many indicator dyes fail to provide consistent and reproducible results.

BRIEF SUMMARY OF THE INVENTION

In an embodiment, the invention provides a method for measuring concentration of an anionic polymer in an aqueous solution, the method comprising (a) combining an indicator dye composition comprising an acridine compound or salt thereof and an aqueous solution to form a mixture, (b) measuring absorbance of the mixture, and (c) comparing the absorbance of the mixture with a calibration curve of absorbance of known concentrations of anionic polymer to determine anionic polymer concentration in the mixture.

In another embodiment, the invention provides a method for measuring concentration of an anionic polymer in an aqueous solution, the method comprising (a) combining an indicator dye composition and an aqueous solution to form a mixture, (b) measuring absorbance of the mixture, and (c) comparing the absorbance of the mixture with a calibration curve of absorbance of known concentrations of anionic polymer to determine anionic polymer concentration in the mixture. The indicator dye composition comprises an acridine compound or salt thereof and a buffer.

In another embodiment, the invention provides a method for measuring concentration of an anionic polymer in an aqueous solution, the method comprising (a) combining an indicator dye composition and an aqueous solution to form a mixture, (b) measuring absorbance of the mixture, and (c) comparing the absorbance of the mixture with a calibration curve of absorbance of known concentrations of anionic polymer to determine anionic polymer concentration in the mixture. The indicator dye composition comprises an acridine compound or salt thereof and a phosphonic acid or salt thereof.

DETAILED DESCRIPTION OF THE INVENTION

The following definitions are provided to determine how terms used in this application, and in particular, how the claims are to be construed. The organization of the definitions is for convenience only and is not intended to limit any of the definitions to any particular category.

"Alkoxy" refers to a moiety of the formula RO—, where R is alkyl;

"Alkyl" refers to a straight-chain or branched alkyl substituent. Examples of such substituents include methyl, ethyl, propyl, isopropyl, n-butyl, sec-butyl, isobutyl, tert-butyl, pentyl, isoamyl, hexyl, and the like;

"Alkylthio" refers to a moiety of the formula RS—, where R is alkyl, aryl, alkenyl, or alkynyl;

"Amino" refers to the moiety $H_2N$—;

"Aminoalkyl" refers to a moiety of the formula RHN— or $R_2N$—, where R is alkyl, benzyl, or aryl;

"Aryl" refers to a moiety of the formula Ar—, where Ar is an aromatic unit;

"Automatic" and "automatically" mean without human intervention or substantially without human intervention. For example, a process carried out automatically (i.e., an "automated process") would measure a variable and take action based on a comparison of the measured variable to a standard value without a person having to do anything to make the action take place, outside of initially providing all necessary equipment, chemical ingredients, and so forth;

"Halogen" or "halo" refers to a moiety selected from the group consisting of F, Cl, Br, and I;

"Halosubstituted alkyl" refers to an alkyl group as described above substituted with one or more halogens, for example, chloromethyl, trifluoromethyl, 2,2,2-trichloroethyl, and the like;

"Heteroaryl" refers to a monocyclic or bicyclic 5- or 6-membered ring system as described herein, wherein the heteroaryl group is unsaturated and satisfies Hückel's rule. Non-limiting examples of suitable heteroaryl groups include furanyl, thiophenyl, pyrrolyl, pyrazolyl, imidazolyl, 1,2,3-triazolyl, 1,2,4-triazolyl, isoxazolyl, oxazolyl, isothiazolyl, thiazolyl, 1,3,4-oxadiazol-2-yl, 1,2,4-oxadiazol-2-yl, 5-methyl-1,3,4-oxadiazole, 3-methyl-1,2,4-oxadiazole, pyridinyl, pyrimidinyl, pyrazinyl, triazinyl, benzofuranyl, benzothiophenyl, indolyl, quinolinyl, isoquinolinyl, benzimidazolyl, benzoxazolinyl, benzothiazolinyl, quinazolinyl, and the like;

"Indicator dye" refers to a compound that can indicate the presence or concentration of a species via analysis of its spectroscopic change;

"Indicator dye composition" refers to a composition comprising an indicator dye, alone or in combination with another component or components;

"Industrial water system" means any system that circulates water as its primary ingredient. Examples of "industrial water systems" may include cooling systems, heating systems, membrane systems, paper making process or any other system that circulates water as defined below;

"Polymer" means homopolymer, copolymer, or any organic chemical composition made up of bonded repeating "mer" units unless the particular context makes clear that one species is intended;

"Scaling" refers to accumulation of undesired material on solid surfaces contacted by water of a water system, or undesired material suspended in a water system;

"Water" means any substance that has water as a primary ingredient. Water may include pure water, tap water, fresh water, brine, steam, and/or any chemical, solution, or blend.

The present invention is directed to a method of using acridine compounds to measure anionic polymer levels in industrial water systems. Acridine compounds, which are commonly used as nucleic-acid selective fluorescent dyes and as indicator dyes for differentiation of DNA from RNA, have been found to strongly interact with anionically charged polymers. Interaction between an acridine compound and an anionic polymer produces a spectroscopic response that can be used to determine the quantity of anionic polymer in a sample. While not wishing to be bound by any particular theory, it is believed that the protonated form of an acridine compound can interact with the anionic sites of the polymer to form ionic complexes, which causes a change in the absorbance of the acridine compound. The absorbance change directly or nearly directly correlates with the amount of polymer present in the water system and can be used to determine the concentration of anionic polymer in aqueous samples. It has been found that acridine indicator dyes yield a broad absorbance range and thus provide exemplary concentration measurement accuracy.

In an embodiment, the invention provides a method for measuring concentration of an anionic polymer in an aqueous solution, the method comprising (a) combining an indicator dye composition comprising an acridine compound or salt thereof and an aqueous solution to form a mixture, (b) measuring absorbance of the mixture, and (c) comparing the absorbance of the mixture with a calibration curve of absorbance of known concentrations of anionic polymer to determine anionic polymer concentration in the mixture.

In another embodiment, the invention provides a method for measuring concentration of an anionic polymer in an aqueous solution, the method comprising (a) combining an indicator dye composition and an aqueous solution to form a mixture, (b) measuring absorbance of the mixture, and (c) comparing the absorbance of the mixture with a calibration curve of absorbance of known concentrations of anionic polymer to determine anionic polymer concentration in the mixture. The indicator dye composition comprises an acridine compound or salt thereof and a buffer.

In another embodiment, the invention provides a method for measuring concentration of an anionic polymer in an aqueous solution, the method comprising (a) combining an indicator dye composition and an aqueous solution to form a mixture, (b) measuring absorbance of the mixture, and (c) comparing the absorbance of the mixture with a calibration curve of absorbance of known concentrations of anionic polymer to determine anionic polymer concentration in the mixture. The indicator dye composition comprises an acridine compound or salt thereof and a phosphonic acid or salt thereof.

The indicator dye composition of the present invention may include an indicator dye (i.e., acridine compound) alone or in combination with one or more additional components (e.g., buffer or chelant).

The indicator dye composition of the present invention comprises an acridine compound. In certain embodiments, the indicator dye composition comprises at least one acridine compound of the following structure:

wherein X, Y, and Z are the same or different and selected from the group consisting of hydrogen, deuterium, alkyl, amino, aminoalkyl, alkoxy, hydroxyl, alkylthio, thiol, aryl, heteroaryl, alkenyl, alkynyl, benzyl, halogen, halosubstituted alkyl, cyano, nitro, and sulfonyl;

wherein X and Y can be located at any position on the acridine ring; and m and n are individually 1, 2, 3, or 4.

In certain preferred embodiments, the indicator dye composition comprises an acridine compound selected from the group consisting of acridine orange, acridine yellow, proflavine, 9-aminoacridine, and salts thereof. In certain preferred embodiments, the indicator dye composition comprises acridine orange or a salt thereof. In certain preferred embodiments, the indicator dye composition comprises acridine orange hemi(zinc chloride) salt (i.e., 3,6-bis(dimethylamino)acridine hydrochloride zinc chloride double salt).

The concentration of the acridine compound is not limited and may depend on the water sample under analysis. In certain embodiments, in order to determine the amount of anionic polymer in a water sample, the aqueous sample is combined with an indicator dye composition comprising an acridine compound at a concentration of from about 0.01 ppm to about 100 ppm. In certain preferred embodiments, the acridine compound is present in the indicator dye composition at a concentration of from about 0.01 ppm to about 50 ppm. In certain preferred embodiments, the acridine compound is present in the indicator dye composition at a concentration of from about 0.01 ppm to about 40 ppm.

In certain preferred embodiments, the acridine compound is present in the indicator dye composition at a concentration of from about 0.01 ppm to about 20 ppm. In certain preferred embodiments, the acridine compound is present in the indicator dye composition at a concentration of from about 0.01 ppm to about 10 ppm. In certain preferred embodiments, the acridine compound is present in the indicator dye composition at a concentration of from about 4 ppm to about 9 ppm. The concentration range of from about 4 ppm to about 9 ppm provides good linearity for polymer concentration measurements, especially for measurement of anionic polymer at a concentration of from about 0.6 ppm to about 20 ppm or more. Thus, in certain preferred embodiments, the indicator dye composition comprises an acridine compound at a concentration of from about 4 ppm to about 9 ppm, from about 4 ppm to about 8 ppm, from about 4 ppm to about 7 ppm, from about 4 ppm to about 6 ppm, from about 5 ppm to about 9 ppm, from about 5 ppm to about 8 ppm, from about 5 ppm to about 7 ppm, from about 6 ppm to about 9 ppm, from about 6 ppm to about 8 ppm, or from about 7 ppm to about 9 ppm.

To determine the concentration of anionic polymer in an aqueous solution, a calibration curve is prepared for each polymer of interest by preparing samples of water having a known concentration of anionic polymer, adding an indicator dye to the sample, and measuring the absorbance of the sample in the presence of the indicator dye. The calibration curve is a plot of absorbance difference vs. known concentration of anionic polymer. Absorbance difference is the difference between the absorbance of the indicator dye by itself and the absorbance of the mixture of indicator dye and the sample of water being tested. The calibration curve can be used to determine the concentration of anionic polymer in a sample by comparing the measured absorbance difference of the sample with the curve and reading the amount of polymer present off of the curve.

The analysis can be performed using any suitable instrument capable of measuring absorbance. In certain preferred embodiments, the instrument used to measure absorbance is a suitable benchtop, portable, or industrial spectrophotometer or colorimeter. The instrument typically comprises a light source, aperture, color filters, and detector configured to measure absorbance as known in the art. In a certain preferred embodiment, colorimetric analysis is carried out using a light source capable of shining light at a particular wavelength, or range thereof, into a sample of anionic polymer containing solution or the anionic polymer-indicator dye composition mixture of the present invention. Comparison of the measured absorbance with the appropriate calibration curve can be conducted manually or automatically using a suitable instrument (e.g., spectrophotometer or colorimeter) to determine the concentration of anionic polymer.

The anionic polymer concentration can be measured using any suitable procedure. For example, in order to determine the concentration of anionic polymer in a sample of water, about 1 mL of the water sample is combined with about 25 mL of an aqueous indicator dye composition. Before the water sample is combined with the indicator dye composition, the water sample is optionally filtered. The preferred filter is an about 0.45-micron filter. The water sample and aqueous indicator dye composition may be measured out using conventional pipettes or pre-calibrated vials. It is possible to conduct the instant method by adding the about 25 mL of aqueous indicator dye composition to the about 1 mL of water sample; however, it is preferred that the about 1 mL of water sample be added to about 25 mL of the aqueous indicator dye composition because this facilitates measuring. The indicator dye composition is preferably an aqueous solution when combined with the water sample.

The anionic polymer in the sample is then allowed to react with the indicator dye composition for any suitable amount of time. In certain preferred embodiments, the reaction time required to determine the concentration of anionic polymer in a sample is less than about 10 minutes. Thus, in certain preferred embodiments, the reaction time required to determine the concentration of anionic polymer in a sample is less than about 10 minutes, less than about 9 minutes, less than about 8 minutes, less than about 7 minutes, less than about 6 minutes, less than about 5 minutes, less than about 4 minutes, less than about 3 minutes, less than about 2 minutes, less than about 1 minute, or less than about 30 seconds. It has been found that the reaction is usually complete in about 30 seconds, making any absorbance measurement taken at about 30 seconds and thereafter accurate. It has been found that this accurate absorbance measurement remains essentially stable for about 15 minutes, with minor fluctuations occurring after the first 2 minutes.

In certain embodiments, the method of measuring concentration of an anionic polymer is an automated method. In other words, the method steps are carried out automatically or nearly automatically, i.e., without or with only minimal human intervention. The calibration curve equation is used by the instrument to calculate the concentration of anionic polymer in the sample. In certain embodiments, the only human intervention required is the minimal act of replacing depleted ingredients and programming the calibration curve into the instrumentation. In certain embodiments, the automated measurement of anionic polymer concentration can be used to optionally control dosage of anionic polymer into the industrial water system.

An advantage of the present invention is that acridine compounds generally have a long shelf-life and are quite stable in solution. For example, the absorbance decay of acridine orange is much slower than the absorbance decay of some commonly used indicator dyes.

Another advantage of the present invention is that acridine compounds have good linear response when used to measure anionic polymer concentration. Thus, the present invention provides a calibration curve having a linear relationship or essentially linear relationship between absorbance and concentration of anionic polymer. Without wishing to be bound by any particular theory, it is believed that the present invention provides a linear or essentially linear calibration curve due to strong interactions between the acridine compound and anionic polymer. In certain preferred embodiments, the calibration curve has an $R^2$ of about 0.98 or more. In certain preferred embodiments, the calibration curve has an $R^2$ of about 0.99 or more.

In certain embodiments, the acridine compound has an absorbance maximum of about 490 nm or less.

In certain embodiments, the acridine compound exhibits a negative response in the presence of anionic polymer, i.e., the absorbance of the acridine decreases with an increase in anionic polymer concentration.

In certain embodiments, the acridine compound is a visual indicator dye. For example, acridine orange typically has a deep orange appearance. However, in certain embodiments, acridine orange has a lighter orange appearance in the presence of increasing amounts of anionic polymer. Thus, visual color change can be used to monitor the presence of anionic polymer. A color comparator can be used to facilitate visual detection of the anionic polymer.

As discussed above, the indicator dye composition is combined with an aqueous solution (i.e., water sample) to determine the amount of anionic polymer in the solution. In certain embodiments, the indicator dye composition is added to the water sample. In certain preferred embodiments, the water sample is added to the indicator dye composition. However, the order of addition does not substantially affect the accuracy of measurement of anionic polymer.

The indicator dye composition can be in any suitable form when combined with the water sample. In certain preferred embodiments, the indicator dye composition is an aqueous solution when combined with the water sample. In certain embodiments, the indicator dye composition is a solution comprising a solvent miscible with water. Those skilled in the art will appreciate that the reaction time required to determine the concentration of anionic polymer in a sample is reduced when the indicator dye composition is an aqueous solution when combined with the water sample. However, the indicator dye composition may be a solid or dry powder when combined with the water sample.

Depending on the pH, an acridine compound may exist as the unprotonated form, the protonated form, or a mixture of both prototropic forms. For example, acridine orange exists essentially as the ionic form at a pH of about 7. While not wishing to be bound by any particular theory, the ionic form of the acridine compound is believed to form a complex with the anionic polymer. Moreover, the anionic polymer is preferably in its unprotonated form so that the anionic portion of the polymer is available to interact with the cationic acridine compound, which generally occurs at non-acidic pH. In certain preferred embodiments, the indicator dye composition is a solution having a pH of from about 6 to about 8. In certain preferred embodiments, the indicator dye composition is a solution having a pH of about 7. However, the indicator dye composition may be a solution having any suitable pH.

In certain preferred embodiments, the indicator dye composition comprises a buffer to maintain pH. In certain embodiments, the buffer is capable of buffering and maintaining a pH of from about 6 to about 8. In certain preferred embodiments, the buffer is capable of buffering and maintaining a pH of about 7. The buffer preferably comprises a weak acid, such as citric acid. Acids such as acetic acid, formic acid, phthalic acid, oxalic acid, and succinic acid may also be used. In certain embodiments, the buffer comprises a mixture of citric acid or a salt thereof and phosphoric acid or a salt thereof. In certain preferred embodiments, the buffer comprises a mixture of citric acid and an alkali metal dihydrogen phosphate salt. In certain preferred embodiments, the buffer comprises a mixture of citric acid and sodium dihydrogen phosphate. In certain embodiments, the buffer comprises citric acid and an alkali metal dihydrogen phosphate salt at a ratio of from about 1:1 to about 1:4.

The indicator dye composition can comprise buffer in any suitable amount. The buffer is preferably added to the indicator dye composition prior to combining the dye with the aqueous solution (e.g., water sample), but may also be added to the water sample prior to combining with the indicator dye composition.

In certain embodiments, the indicator dye composition comprises a chelant. In certain embodiments, the chelant is a phosphonic acid or salt thereof. In certain preferred embodiments, the indicator dye composition comprises 2-phosphonobutane-1,2,4-tricarboxylic acid or a salt thereof (e.g., ammonium or alkali metal salt). In certain preferred embodiments, the chelant is 2-phosphonobutane-1,2,4-tricarboxylic acid sodium salt. The 2-phosphonobutane-1,2,4-tricarboxylic acid sodium salt can be pre-formed or prepared in situ by reacting 2-phosphonobutane-1,2,4-tricarboxylic acid with an appropriate amount of NaOH prior to formation of the indicator dye composition. In certain embodiments, the indicator dye composition is a solution comprising 2-phosphonobutane-1,2,4-tricarboxylic acid or a salt thereof and has a pH of from about 6 to about 8. In certain preferred embodiments, the indicator dye composition is a solution comprising 2-phosphonobutane-1,2,4-tricarboxylic acid or a salt thereof and has a pH of about 7. The inclusion of 2-phosphonobutane-1,2,4-tricarboxylic acid or a salt thereof in the indicator dye composition provides calibration curves having a slightly higher linearity when compared to calibration curves prepared using a citrate-based buffer.

The indicator dye composition can comprise chelant in any suitable amount. The chelant is preferably added to the indicator dye composition prior to combining the dye with the water sample, but may also be added to the water sample prior to combining with the indicator dye composition.

It is well known to those in the art that indicator dyes can be susceptible to decomposition under certain conditions (e.g., in the presence of oxygen). Chemical treatments can be used to reduce the level of oxygen in the water system. In certain embodiments, an oxygen scavenger can be used to limit the amount of oxygen in the water system to reduce or prevent decomposition of the acridine compound. Representative oxygen scavengers include, but are not limited to, sodium sulfite, hydrazine, tannin, erythorbic acid, salts thereof, or combinations thereof. The oxygen scavenger is preferably added to the indicator dye composition prior to combining the dye with the water sample, but may also be added to the water sample prior to combining with the indicator dye composition. In certain embodiments, the oxygen scavenger may be added after the indicator dye composition and water sample have been combined.

An advantage of the present invention is that, in certain embodiments, contaminant ions commonly found in industrial water systems do not interfere with accurate measurement of anionic polymer. Applicant has discovered that acridine compounds can have low susceptibility to contaminant interference, particularly in the presence of calcium and magnesium ions. In other embodiments, alkali bivalent salts, oxygen scavengers, and masking agents may be necessary to reduce interference of contaminant ions with the measurement of anionic polymer.

As discussed above, anionic polymers are widely used in industrial water systems to inhibit scale formation and remove existing scale. Such anionic polymer classes include polyacrylates, polymethacrylates, polymaleic acid, sulfonated polymers, carboxylated polymers, and carboxymethylcellulose, and copolymers thereof. Representative anionic polymers include poly(acrylic acid) and its salts, formed from monomers including but not limited to, sodium acrylate, and ammonium acrylate, methacrylic acid, and its salts, including, but not limited to sodium methacrylate, and ammonium methacrylate, 2-acrylamido-2-methylpropanesulfonic acid, the sodium salt of 2-acrylamido-2-methylpropanesulfonic acid, sodium vinyl sulfonate, styrene sulfonate, maleic acid, and its salts, including, but not limited to the sodium salt, and ammonium salt, sulfonate itaconate, sulfopropyl acrylate or methacrylate or other water-soluble forms of these or other polymerizable carboxylic or sulphonic acids. Other representative anionic monomers include sulfomethylated acrylamide, allyl sulfonate, sodium vinyl sulfonate, itaconic acid, acrylamidomethylbutanoic acid, fumaric acid, vinylphosphonic acid, vinylsulfonic acid, allylphosphonic acid, sulfomethylated acrylamide, phosphonomethylated acrylamide, and the like.

In certain preferred embodiments, the anionic polymer comprises poly(acrylic acid). In certain preferred embodiments, the anionic polymer comprises a poly(amide). In certain preferred embodiments, the anionic polymer comprises a sulfomethylated acrylamide monomer.

In certain embodiments, an indicator dye composition can be used to effectively measure polymers at relatively low concentration. While any amount of anionic polymer can be measured using the present invention, in certain preferred embodiments, the present invention is used to measure anionic polymer at a concentration of from about 0.1 ppm to about 100 ppm. Thus, in certain preferred embodiments, the anionic polymer is at a concentration of from about 0.1 ppm to about 100 ppm, from about 0.5 ppm to about 100 ppm, from about 1 ppm to about 100 ppm, from about 5 ppm to about 100 ppm, from about 0.1 ppm to about 50 ppm, from about 0.1 ppm to about 25 ppm, from about 0.1 ppm to about 20 ppm, from about 0.1 ppm to about 10 ppm, from about 0.5 ppm to about 50 ppm, from about 0.5 ppm to about 25 ppm, from about 0.5 to about 20 ppm, from about 0.5 to about 10 ppm, from about 1 ppm to about 50 ppm, from about 1 ppm to about 25 ppm, from about 1 ppm to about 20 ppm, or from about 1 ppm to about 10 ppm. The dosage of anionic polymer can be optionally adjusted based on the measured concentration.

The anionic polymer can be of any molecular weight. In certain embodiments, the anionic polymer has a molecular weight of from about 500 Daltons to about 20,000 Daltons. In certain preferred embodiments, the anionic polymer has a molecular weight of from about 500 Daltons to about 10,000 Daltons. Thus, in certain preferred embodiments, the anionic polymer has a molecular weight of from about 500 Daltons to about 10,000 Daltons, from about 1,000 Daltons to about 10,000 Daltons, from about 500 Daltons to about 5,000 Daltons, from about 500 Daltons to about 2,000 Daltons, or from about 1,000 Daltons to about 5,000 Daltons.

In certain preferred embodiments, the present invention is used to determine the concentration of anionic polymer in a cooling water system or boiler system.

In certain embodiments, the indicator dye composition includes one or more acridine compounds.

In an embodiment, a kit for measuring concentration of an anionic polymer comprises an indicator dye composition comprising an acridine compound or salt thereof and instructions for combining the indicator dye composition and an aqueous solution to measure the concentration of the anionic polymer. The kit may further comprise a buffer, chelant, vial, pipet, and/or spectrophotometer or colorimeter.

The following examples further illustrate the invention but, of course, should not be construed as in any way limiting its scope.

EXAMPLE 1

This Example illustrates the construction and linearity of a calibration curve for an anionic polymer of interest, which plots the absorbance difference vs. known concentration of the anionic polymer.

Accordingly, an acridine orange standard solution was prepared by combining acridine orange hemi(zinc chloride) salt (0.0189 mmol, 7 mg, Sigma-Aldrich) to a neutral pH buffer solution comprising citric acid (1 mL of 0.1M aq.), $Na_2HPO_4$ (2.5 mL of 0.2 M aq.), and 900 mL deionized water. Additional deionized water was added to the solution until the total volume was 1 liter. Anionic polymer standard solutions were prepared separately using known amounts of anionic polymer (0.6 to 20 ppm).

A 1 mL aliquot of each anionic polymer standard solution was added to a 25 mL aliquot of acridine orange standard solution. After 30 seconds, the absorbance of the anionic polymer-acridine orange standard solution and the acridine orange standard solution by itself was measured at 490 nm using a Hach DR 2800 or DR 5000 spectrophotometer. The absorbance difference was calculated by subtracting the absorbance of the mixture of acridine orange and anionic polymer from the absorbance of acridine orange by itself. A plot of absorbance difference vs. known concentration of anionic polymer was prepared.

Figure 1:
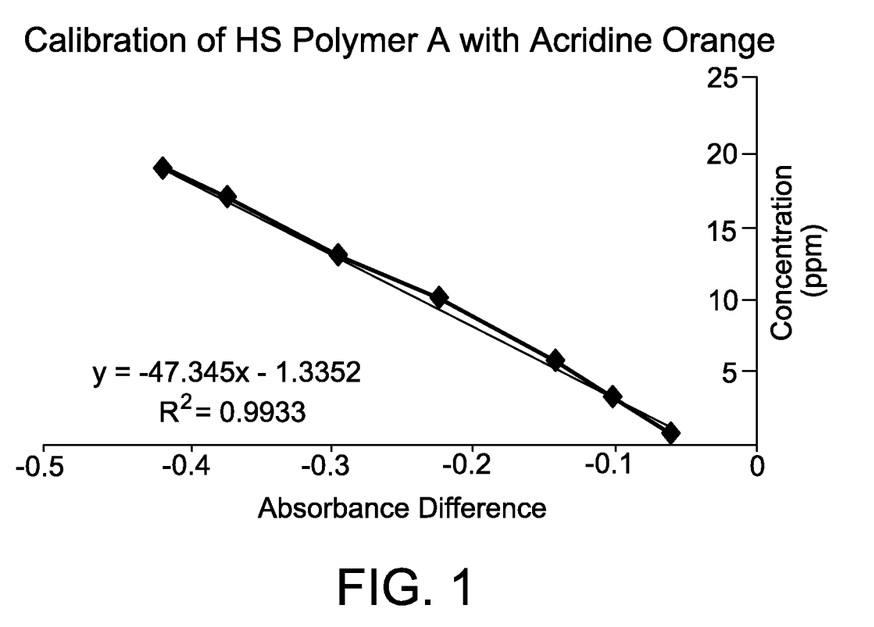
FIG. 1 is a calibration curve displaying absorbance difference vs. concentration of High Stress Polymer A.
Figure 2:
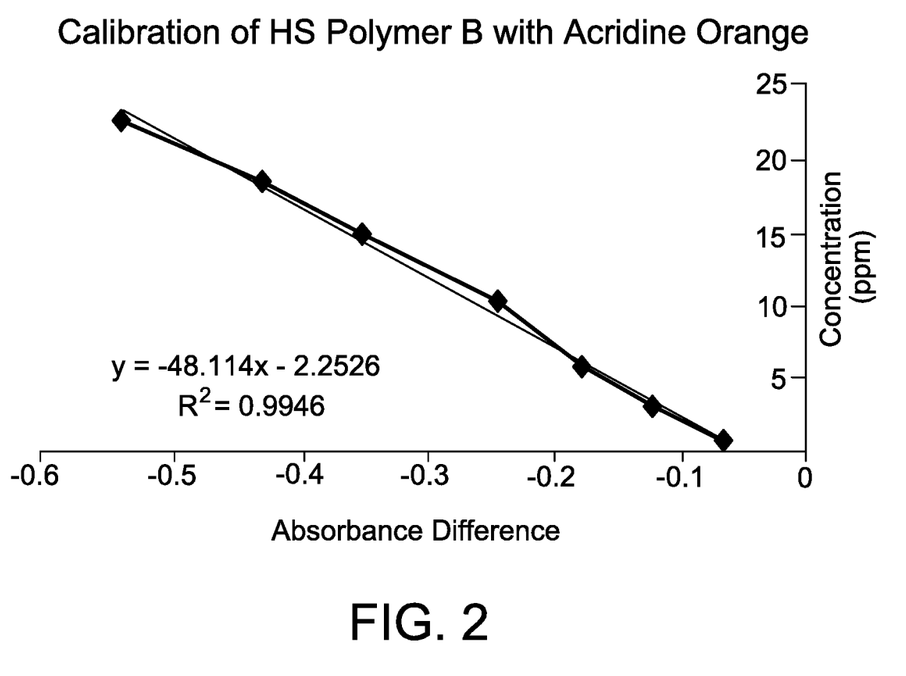
FIG. 2 is a calibration curve displaying absorbance difference vs. concentration of High Stress Polymer B.
Figure 3:
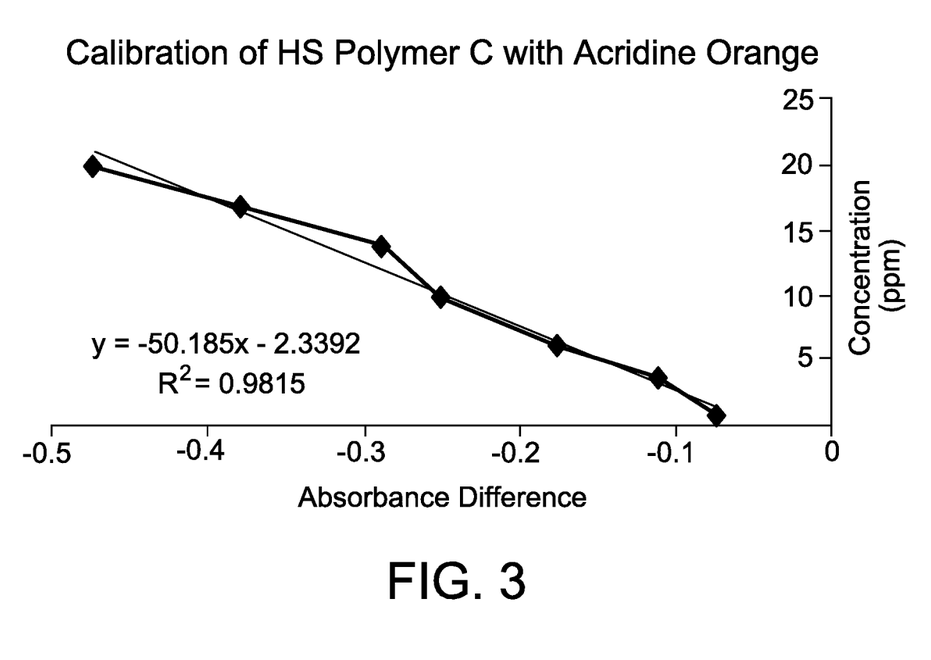
FIG. 3 is a calibration curve displaying absorbance difference vs. concentration of High Stress Polymer C.

Calibration curves are shown for three high stress polymers in FIGS. 1-3, where absorbance difference is plotted along the horizontal axis and the anionic polymer concentration is plotted along the vertical axis.

Overall, the calibration of anionic polymer using acridine orange provides excellent linearity ($R^2$ up to 0.99).

EXAMPLE 2

This Example illustrates the accuracy and reproducibility of an embodiment of the present inventive method.

The accuracy and reproducibility was determined by analyzing aqueous samples comprising a known amount of anionic polymer. The experiment was conducted using acridine orange in the presence of a citrate-based buffer and phosphonobutane-1,2,4-tricarboxylic acid.

Accordingly, an acridine orange standard solution comprising a citrate-based buffer was prepared by combining acridine orange hemi(zinc chloride) salt (0.0189 mmol, 7 mg), citric acid (1 mL of 0.1M aq.), $Na_2HPO_4$ (2.5 mL of 0.2 M aq.), and 900 mL deionized water. Additional deionized water was added to the solution until the total volume was 1 liter. An acridine orange standard solution comprising a phosphonic acid chelant was prepared by combining acridine orange hemi(zinc chloride) salt (0.0189 mmol, 7 mg), phosphonobutane-1,2,4-tricarboxylic acid (PBTC, 0.870 mmol, 0.235 g), and 900 mL deionized water. Additional deionized water was added to the solution until the total volume was 1 liter. The pH was between 7 and 7.3 for both acridine orange standard solutions. If the pH is outside of this range, base (e.g., sodium hydroxide) can be used to adjust the pH to 7-7.3.

A 1 mL aliquot of an aqueous solution comprising a known amount of anionic polymer (10 ppm) was combined with a 25 mL aliquot of acridine orange standard solution comprising citrate buffer. A 1 mL aliquot of an aqueous solution comprising a known amount of anionic polymer (8.61 ppm) was combined with a 25 mL aliquot of acridine orange standard solution comprising phosphonobutane-1,2,4-tricarboxylic acid. After 30 seconds, the absorbance of each solution was measured at 490 nm using a Hach DR 2800 or DR 5000 spectrophotometer. The absorbance difference between the absorbance of an acridine orange standard solution alone and the solution of interest was calculated. The calibration curve was used to determine the concentration of anionic polymer present in the sample. The above procedure was repeated 8 additional times.

As shown in Table 1, the acridine orange in the presence of a chelant or PBTC provided accurate and consistent absorbance and concentration readings for the anionic polymer over multiple runs. Both the acridine orange standard solution comprising a citrate-based buffer and phosphonic acid chelant gave reproducible results, resulting in a % RSD (concentration) of 3.177% and 3.63%, respectively.

Thus, the method of the present invention is an accurate and reproducible method for measuring anionic polymer concentration.

TABLE 1

| | Reproducibility with Citrate Buffer | | | Reproducibility with PBTC | |
|---|---|---|---|---|---|
| Run | Absorbance Difference | Concentration (ppm) | Run | Absorbance Difference | Concentration (ppm) |
| 1 | −0.24 | 10.03 | 1 | −0.221 | 8.43 |
| 2 | −0.246 | 10.31 | 2 | −0.221 | 8.49 |
| 3 | −0.252 | 10.60 | 3 | −0.225 | 8.64 |
| 4 | −0.228 | 9.46 | 4 | −0.219 | 8.33 |
| 5 | −0.237 | 9.89 | 5 | −0.223 | 8.54 |
| 6 | −0.238 | 9.93 | 6 | −0.224 | 8.59 |
| 7 | −0.241 | 10.07 | 7 | −0.224 | 8.59 |
| 8 | −0.236 | 9.84 | 8 | −0.240 | 9.40 |
| 9 | −0.237 | 9.89 | 9 | −0.229 | 8.84 |
| Average | −0.239 | 10.001 | Average | −0.225 | 8.65 |
| Standard Dev. | 0.007 | 0.318 | Standard Dev. | 0.006 | 0.31 |
| % RSD | −2.802 | 3.177 | % RSD | −2.753 | 3.63 |

EXAMPLE 3

This Example examines the effect of major ions on the absorbance of an acridine compound-anionic polymer mixture.

Accordingly, three solutions (Samples A-C) were prepared and analyzed spectroscopically to determine if the presence of calcium, magnesium, and alkalinity would affect the measured absorbance of an acridine orange-anionic polymer mixture.

Accordingly, Samples A-C were prepared and analyzed. Sample A comprised calcium (1700 ppm), magnesium (1700 ppm), and alkalinity (2000 ppm). Sample B comprised anionic polymer (9 ppm). Sample C comprised calcium (1700 ppm), magnesium (1700 ppm), alkalinity (2000 ppm), and anionic polymer (9 ppm). An acridine orange standard solution comprising a phosphonic acid chelant was prepared by combining acridine orange hemi(zinc chloride) salt (0.0189 mmol, 7 mg), phosphonobutane-1,2,4-tricarboxylic acid (PBTC, 0.870 mmol, 0.235 g), and 900 mL deionized water. Additional deionized water was added to the solution until the total volume was 1 liter. The pH of the acridine orange standard solution was between 7 and 7.3. If the pH is outside of this range, base (e.g., sodium hydroxide) can be used to adjust the pH to 7-7.3.

A 1 mL aliquot of Samples A-C was individually added to a 25 mL aliquot of acridine orange standard solution comprising 2-phosphonobutane-1,2,4-tricarboxylic acid. After 30 seconds, the absorbance of Samples A-C was measured at 490 nm using a Hach DR 2800 or DR 5000 spectrophotometer. The absorbance difference between the absorbance of the acridine orange standard solution and Samples A-C was calculated and recorded in Table 2.

As shown in Table 2, there is no substantial difference in absorbance between the sample comprising anionic polymer (Sample B) and the sample comprising both ionic species and anionic polymer (Sample C).

Thus, the presence of major ions does not substantially affect the absorbance of acridine orange-anionic polymer mixtures.

TABLE 2

| Sample | Absorbance Difference |
|---|---|
| Sample A - Ca, Mg, Alk | −0.045 |
| Sample B - Anionic Polymer | −0.210 |
| Sample C - Ca, Mg, Alk, and Anionic Polymer | −0.212 |

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for measuring concentration of an anionic polymer in an aqueous solution, the method comprising:
   contacting a liquid composition comprising (a) an acridine compound or salt thereof, (b) an organic chelant or a citrate buffer, and (c) water with an aqueous solution comprising an anionic polymer to form a mixture;
measuring absorbance of the mixture; and
comparing the absorbance of the mixture with a calibration curve of absorbance of known concentrations of anionic polymer to determine anionic polymer concentration in the mixture.

2. The method of claim 1, wherein the acridine compound is selected from the group consisting of acridine orange, acridine yellow, proflavine, 9-aminoacridine, and salts thereof.

3. The method of claim 2, wherein the acridine orange is acridine orange hemi(zinc chloride) salt.

4. The method of claim 1, wherein the acridine compound is present in the liquid composition at a concentration of from about 0.01 ppm to about 40 ppm.

5. The method of claim 1, wherein the acridine compound is present in the liquid composition at a concentration of from about 0.01 ppm to about 10 ppm.

6. The method of claim 1, wherein the liquid composition is a solution having a pH of from about 6 to about 8.

7. The method of claim 1, wherein the liquid composition is a solution having a pH of about 7.

8. The method of claim 1, wherein anionic polymer concentration is determined with a colorimeter.

9. The method of claim 1, wherein the anionic polymer has a molecular weight of from about 500 Daltons to about 20,000 Daltons.

10. The method of claim 1, wherein the calibration curve has an $R^2$ value of about 0.98 or more when the anionic polymer has a concentration of about 20 ppm or less.

11. A method for measuring concentration of an anionic polymer in an aqueous solution, the method comprising:
contacting a liquid composition comprising an acridine compound or salt thereof and water with an aqueous solution comprising an anionic polymer comprising a poly(acrylamide) to form a mixture;
measuring absorbance of the mixture; and
comparing the absorbance of the mixture with a calibration curve of absorbance of known concentrations of anionic polymer to determine anionic polymer concentration in the mixture.

12. The method of claim 11, wherein the acridine compound is selected from the group consisting of acridine orange, acridine yellow, proflavine, 9-aminoacridine, and salts thereof.

13. The method of claim 11, wherein the liquid composition further comprises a citrate, a phosphoric acid or a salt thereof, or a combination thereof.

14. The method of claim 11, wherein the liquid composition further comprising a phosphonic acid or a salt thereof.

15. A method for measuring concentration of an anionic polymer in an aqueous solution, the method comprising:
contacting a liquid composition comprising (a) an acridine compound or salt thereof,(b) a phosphonic acid or a salt thereof, and (c) water with an aqueous solution comprising an anionic polymer to form a mixture;
measuring absorbance of the mixture; and
comparing the absorbance of the mixture with a calibration curve of absorbance of known concentrations of anionic polymer to determine anionic polymer concentration in the mixture.

16. The method of claim 15, wherein the acridine compound is selected from the group consisting of aeridine orange, acridine yellow, proflavine, 9-aminoacridine, and salts thereof.

17. The method of claim 15, wherein the phosphoric acid is 2-phosphonobutane-1,2,4-tricarboxylic acid or a salt thereof.

18. The method of claim 15, wherein the liquid composition is a solution having a pH of from about 6 to about 8.

19. The method of claim 15, wherein the calibration curve has an $R^2$ value of about 0.98 or more when the anionic polymer has a concentration of about 20 ppm or less.

* * * * *

UNITED STATES PATENT AND TRADEMARK OFFICE
CERTIFICATE OF CORRECTION

PATENT NO. : 9,599,566 B2  
APPLICATION NO. : 15/088609  
DATED : March 21, 2017  
INVENTOR(S) : Hua Zheng Page 1 of 1

It is certified that error appears in the above-identified patent and that said Letters Patent is hereby corrected as shown below:

At Column 14, Line 7, change "yellow,proflavine," to --yellow, proflavine,--

At Column 14, Line 18, change "thereof;(b)" to --thereof; (b)--

At Column 14, Line 27, change "aeridine" to --acridine--

Signed and Sealed this  
Thirteenth Day of June, 2017

Joseph Matal  
*Performing the Functions and Duties of the*  
*Under Secretary of Commerce for Intellectual Property and*  
*Director of the United States Patent and Trademark Office*